United States Patent [19]
Bennett

[11] Patent Number: 5,427,741
[45] Date of Patent: Jun. 27, 1995

[54] PRESSURE RESISTANT REINFORCING MEANS FOR CONTAINERS FOR MATERIALS TO BE MICROWAVE HEATED

[75] Inventor: Jonathan P. Bennett, Charlotte, N.C.

[73] Assignee: CEM Corporation, Matthews, N.C.

[21] Appl. No.: 64,753

[22] Filed: May 19, 1993

[51] Int. Cl.⁶ .......................... B01L 3/00; G01N 25/00
[52] U.S. Cl. ..................................... 422/102; 219/756; 422/78; 422/104; 428/36.3
[58] Field of Search .................. 422/102, 103, 78, 99, 422/113; 219/10.55 E; 428/36.3, 36.6

[56] References Cited

U.S. PATENT DOCUMENTS

| | | | |
|---|---|---|---|
| 4,200,482 | 4/1980 | Magerle | 156/443 |
| 4,228,208 | 10/1980 | Smith et al. | 428/95 |
| 4,353,763 | 10/1982 | Simons | 156/184 |
| 4,507,338 | 3/1985 | Freundlich | 428/36.5 |
| 4,865,787 | 9/1989 | Vallance et al. | 264/101 |
| 4,882,128 | 11/1989 | Hukvari et al. | 422/119 |
| 4,882,286 | 11/1989 | Neas et al. | 436/175 |
| 4,886,699 | 12/1989 | Carroll et al. | 428/228 |
| 4,904,450 | 2/1990 | Floyd | 422/78 X |
| 4,933,526 | 6/1990 | Fisher et al. | 219/10.55 M |
| 4,950,532 | 8/1990 | Das et al. | 428/290 |
| 5,190,809 | 3/1993 | Marissen et al. | 428/225 |
| 5,204,065 | 4/1993 | Floyd | 422/113 |
| 5,230,865 | 7/1993 | Hargett et al. | 422/102 |

OTHER PUBLICATIONS

Atkins & Pearce Silasox Date Sheet, 1 page, Jan. 1991.
Miller, W. A. "How to choose a flluropolymer", *Chemical Engineering,* pp. 163–167, Apr. 1993.
Owens Corning S-2 Glass Fiber Pub'n., 2 pages, date unknown, enclosed.
Dupont Teflon PFA Data Sheet, 1 page, date unknown, enclosed.
GE Plastics ULTEM 1000 Data Sheets, 3 pages, date unknown, enclosed.
Dupont Kevlar Aramid Publication, 15 pages, date unknown, enclosed.

*Primary Examiner*—Robert J. Warden
*Assistant Examiner*—Robert Carpenter
*Attorney, Agent, or Firm*—Raymond F. Kramer

[57] ABSTRACT

Containers for materials which are to be microwave heated such as in digesting or extracting operations, are made of thermoplastic material, such as a fluoropolymer, e.g., TEFLON ® PFA, that is strengthened by reinforcing means that may be a fiber reinforced thermoplastic of high tensile strength, such as polyetherimide, e.g., ULTEM ®, with reinforcing continuous fibers in a matrix of such thermoplastic, which fibers are preferably of glass or other heat resistant and microwave transmissive material. The containers may be strengthened by incorporating the fiber reinforced thermoplastic in a wall or walls of the container or by inserting the container into a reinforcement, which is a sleeve or collar of the reinforced thermoplastic. In both such constructions the reinforcing means protects the container against peripheral or radial failure due to pressure that is generated by the microwave heating of the container contents. Also described are processes for manufacturing the described reinforcing means and for utilizing containers protected by such means.

1 Claim, 7 Drawing Sheets

PRESSURE RESISTANT REINFORCING MEANS FOR CONTAINERS FOR MATERIALS TO BE MICROWAVE HEATED

This invention relates to pressure resistant reinforcing means for containers that may be subjected to high internal pressures during microwave heating of their contents. More particularly, the invention is of reinforced walls of such containers and of reinforcements for the containers that act as confining means or sleeves to prevent failures of the container walls and burstings of the containers when the internal pressures and temperatures of the containers are raised, such as to 600 lbs./sq. in. (or 42 kg./sq. cm.) and 400° F. (or 204° C.). In a broader sense the invention relates to continuous fiber-reinforced tubular structures that are comprised of a thermoplastic that is reinforced against peripheral or radial failure by continuous microwave transmissive fibers that are enclosed in a matrix of the thermoplastic.

It has been known in the art that plastics may be reinforced by forming them about reinforcing fibrous materials, such as glass fibers. Rocket engine parts, which are subject to high temperatures and pressures and to consequent strains in operation, have been formed of graphite fiber reinforced thermosetting polymers, which fibers may be in continuous yarn or weave form. Containers for materials that are to be stored under pressure have been made from fiberglass-reinforced polyesters and containers made from plastics that are not so reinforced have been reinforced with surrounding sleeves. In fiber-reinforced containers the presence of the fibrous material has contributed strength to the thermoset plastic matrix material. However, thermosetting plastics, such as phenolics, polyesters, epoxies silicones, alkyds, melamines and diallylphthalates, are not microwave transmissive and therefore are unsuitable for use as materials of construction for containers that are to be subjected to microwave radiation. In addition, containers for materials that are to be digested or extracted, utilizing microwave heating, often should be resistant to attack by strong acids and organic solvents. It has been found by the present inventor that fluoropolymers, such as those described in *Chemical Engineering* for April, 1993, in an article beginning at page 163, which are melt processable, many of which have been sold under the E.I. DuPont de Nemours, Inc. trademark TEFLON®, which may hereafter be referred to as fluoropolymers or PFA (which is the designation for a preferred such fluoropolymer), possess the desired acid and solvent resistances and other physical properties which make them suitable for the present applications, but they are not of sufficient tensile strength at elevated temperatures to be useful as unreinforced materials of construction for containers to be subjected to elevated pressures, such as those previously mentioned herein. Polyetherimides, such as those sold under the trademark ULTEM®, of General Electric Company, Inc., while not themselves sufficiently resistant to attacks by strong acids and organic solvents to be useful as container interior wall materials, are of greater tensile strengths than such fluoropolymers but are not of sufficiently high strengths to be employable as reinforcing sleeves or other means for protecting digestion or extraction containers of fluoropolymers against failure at elevated temperatures due to very high pressures generated in such containers during microwave heating. However, when strengthened by incorporation therein of continuous glass fibers (or other high tensile strength fibers, such as those of quartz or aramid [sold under the trademark KEVLAR® by E.I. dupont de Nemours, Inc.]), preferably in the form of yarns, braids or sleeves, such polyetherimide-fiber combinations are of satisfactory strengths and can be employed as reinforcing means for containers in accordance with this invention. By "reinforcing means" it is meant to designate such means as may be part or all of a wall of a container (which container will be of or lined with fluoropolymer or other acid and solvent resistant material), or may be a reinforcement (which can surround or encompass a part or all of a container to restrain it and prevent radial or peripheral rupture thereof under internal pressure). Although the described reinforced thermoplastics can be satisfactory reinforcing means for containers to be microwave heated, before the present invention no simple and practicable way was known to make such composites because the thermoplastic solid had to be heated before use to liquefy it, and during processing to the composite by typical "lay-up" techniques uneven coolings and partial solidifications were often encountered, which could lead to products of uneven appearances and heterogeneous compositions, with weak spots that were subject to rupture under pressure, especially at elevated temperatures. Applicant's solution to this problem is to utilize sheets of high tensile strength thermoplastic resin or polymer, such as polyetherimide (PEI), which are wrapped about a mandrel (which is preferably cylindrical in shape) with glass fiber yarn braids or weaves, in sleeve, sheet or other suitable form between them, and heat the composite to the melt temperature of the thermoplastic, at which the thermoplastic fills in any voids between the fibers and yarns and forms inner and outer smooth surfaces on the item, which is then solidified by cooling. However, other processes have since been found to be operative in manufacturing the present reinforcing means and some of them will subsequently be described in this specification.

In accordance with the present invention a reinforcing means for a sealable container for material that is to be heated by microwave radiation, which can raise the pressure in the container, which reinforcing means is at least a part of a wall of said container or at least a part of a reinforcement for said container, comprises a microwave transmissive thermoplastic of a tensile strength at 150° C. of at least 1,000 lbs./sq. in. and continuous reinforcing glass, quartz or aramid fibers or yarns therein, with said fibers or yarns being so located in the thermoplastic as to increase the tensile strength of the thermoplastic to at least 30,000 lbs./sq. in. to prevent rupture of the container wall at temperatures up to 150° C. and internal pressures up to 500 lbs./sq. in. gauge. Said reinforcing means may be a part or all of a wall of a container, such as a curved or cylindrical side of a curved or cylindrical container or may be a reinforcement for part or all of a wall of such a container, which may fit the container and confine it, such as an enclosing cylinder, cylindrical container tube, sleeve or collar. It has been found that for cylindrical or other tubular containers the major forces exerted on the container structure due to internal pressure buildup, when contents of the container are heated, are on the container side walls and not on the ends, so ruptures of such containers occur more frequently at the sides, to avoid which usually requires thicker sides than tops and bottoms, for safe operation under pressure. Also, the ends of the containers include lesser proportions of the container surfaces and can be more easily and practicably thickened or reinforced, as by protective holders, to withstand expected internal pressures. Therefore, it was the applicant's view that to prevent rupturings of containers due to internal pressures generated by heatings of container contents a primary object should be to strengthen or otherwise to protect the container side walls, and that is what the present invention has accomplished. Furthermore, even if the design pressure for the reinforced containers or for the reinforcements of this invention is exceeded, which is highly unlikely, any resulting rupture of the container will not be explosive, as it would be with tional plastic containers, but will be more gradual, due to the presence of the reinforcing means, which will tend to decrease the severity of any damage that might result.

The invention will be readily understood by reference to this specification, including the claims, taken in conjunction with the drawing, in which:

Figure 10:
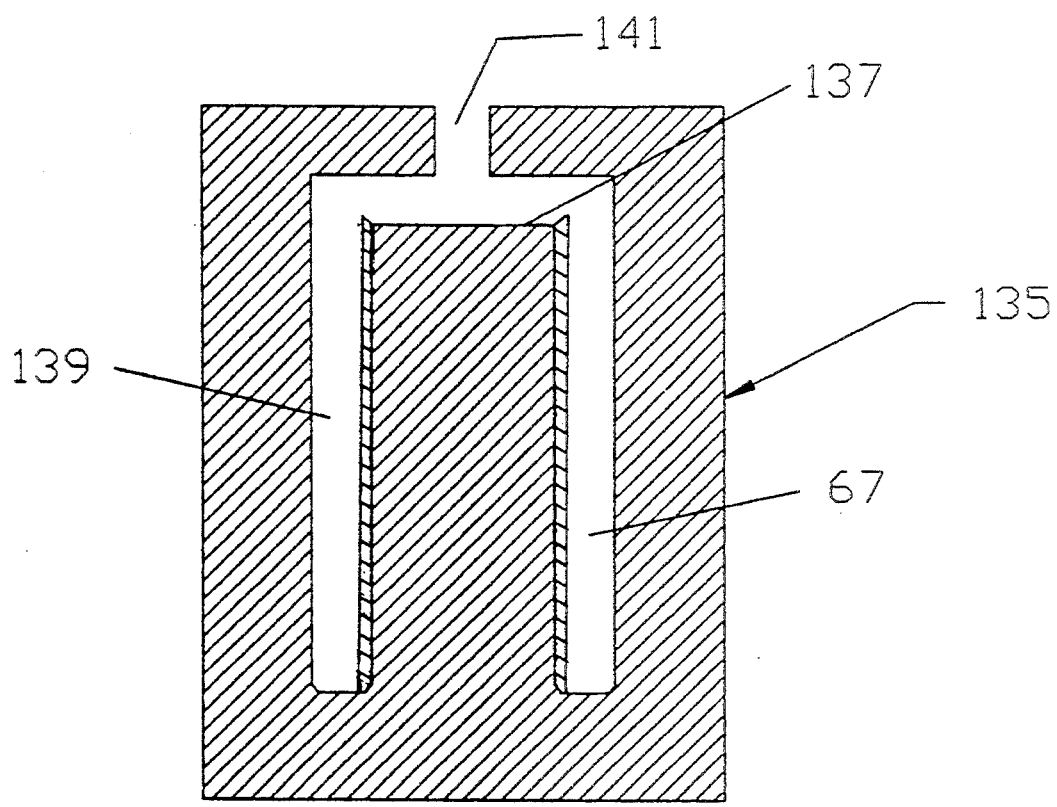
Figure 11:
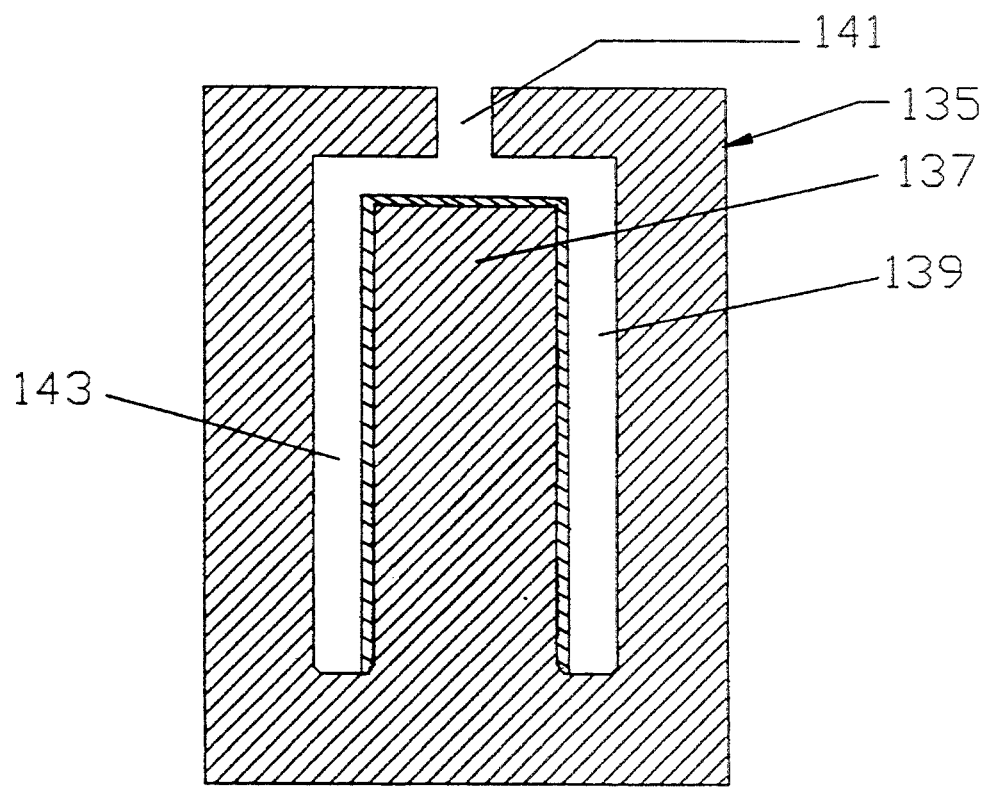

FIG. 10 is a schematic central vertical sectional elevation of a single cavity portion of an injection mold, showing positioning of a continuous fiber reinforced PEI tube therein prior to injection of unreinforced PEI or PFA about it; and FIG. 11 is a view like that of FIG. 10, of a container of this invention, with a bottom thereon of reinforced PEI, joined to a reinforced cylindrical wall, prior to injection of PEI or PFA about it.

Figure 1:
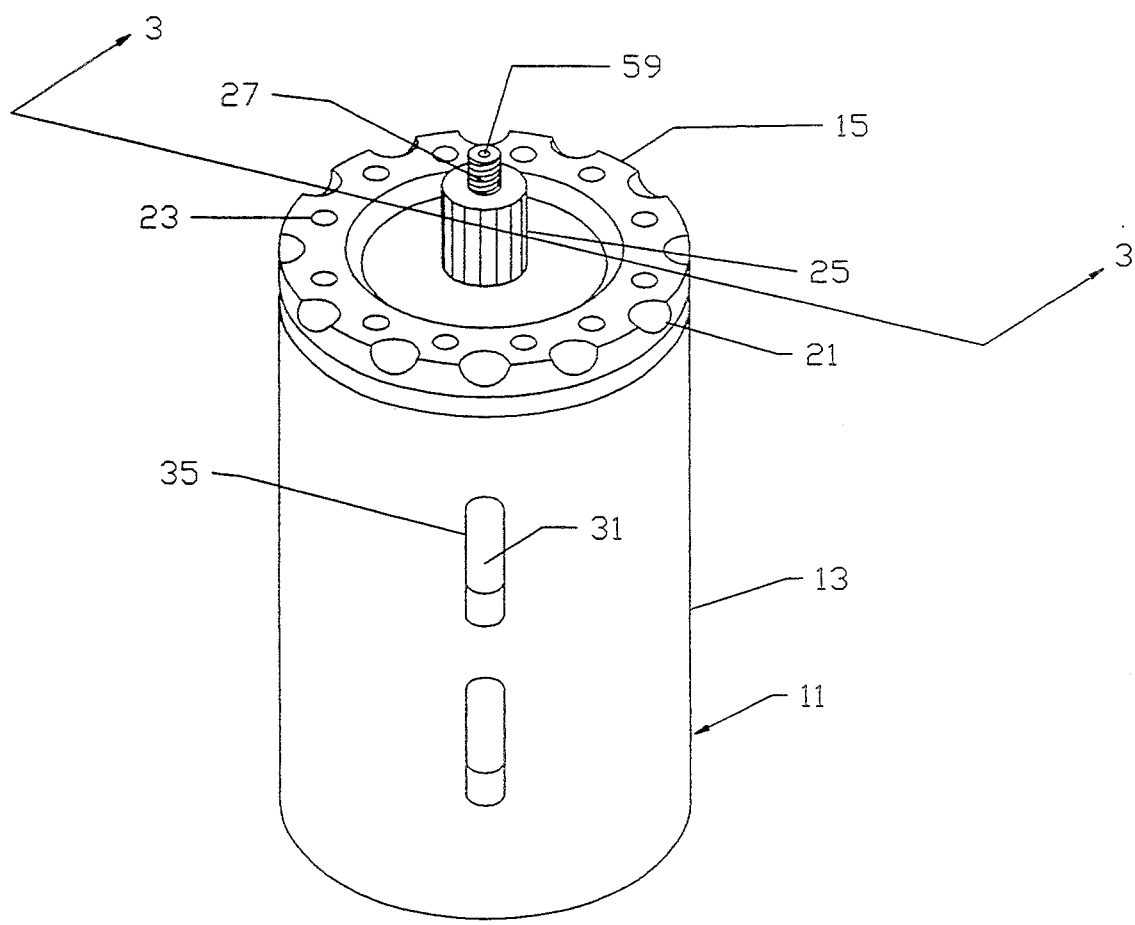
FIG. 1 is a perspective view of an apparatus of this invention viewed from the top front, in which a container for material (not visible) which is to be microwave heated is positioned inside a reinforcement of the invention, with both the container and the reinforcement being retained in position in a holder, which also holds a cover (not visible) onto the container.

In FIG. 1 there is shown holder 11 which includes a body 13 and a cap 15, which cap is threadably fastenable to the body so as to hold a cover 17 (not shown in FIG. 1) to a body portion 18 (not shown in FIG. 1) of a container 19 (also not shown in FIG. 1). Cap 15 has spherical depressions 21 near the top peripheral edge thereof for hand tightening of the cap to the holder body and has cylindrical openings 23 near the outside of the top thereof for tool loosening of the cap after completion of the heating operation. Atop the cap 15 a fitting 25 is positioned, which is internally bored and threaded and has an externally threaded nipple 27, suitable for connection to a sump into which material from container 19 is directed if rupture disc 29 (not shown in FIG. 1) is ruptured due to excessive internal pressure in said container. Alternatively, when expelled, such material may be directed outside the microwave heating chamber, to waste or to other safe place. Fitting 25 is held to cap 15 by an upwardly extending nipple 37 (not shown in FIG. 1) at the top of cover 17, and nipple passageway 38 communicates with the interior of container 19 through a restricted passageway 61 (not shown in FIG. 1) through the container cover. Thus, tightening down of cap 15 onto holder body 13, with fitting 25 in place, seals off container 19, preventing exit of contents unless rupture disc 29 (in fitting 25) fails, due to pressure in the container that is in excess of the maximum for which it is designed. Ultimately, the bottom of the holder and the cap for it bear the axial pressure in the container, and the material of construction of the holder, which may be polypropylene or other suitable material, is of a size (and of a thickness), that can withstand the maximum design pressure (with a safety factor, too) of the container. As is seen from the drawing, the holder is of comparatively large dimensions, including thickness, compared to those of the container. Because the peripheral or radial stress exerted on a tube, such as a cylinder, is essentially twice that of the axial stress (for thin walled containers) if one were to use only a holder with thickened side wall (the curved peripheral wall) to restrain the container side wall and prevent failure thereof at internal container pressures higher than those the container itself could withstand, the holder wall thickness would have to be unacceptably great for the useful materials available (which could also acceptably withstand solvent and chemical attacks by contents). Therefore, the present inventor tried to invent suitable reinforcing means for containers which would be thinner and stronger so that they could be parts of walls (or all of such walls) of containers or of restraining reinforcements for such containers. Such a reinforcement 31, which tightly conforms internally with the external cylindrical wall of container 19, is illustrated in FIGS. 2–5. Between the internal wall of holder body 13 and the external wall of reinforcement 31 is an open space 33 (shown in FIG. 3) which aids air circulation about reinforcement 31 and promotes cooling of container 19 and contents thereof when that is desired. Openings 35 provide access to space 33 and in an embodiment of the invention, illustrated in FIGS. 1–3, six of such openings are provided (although various numbers may be employed for optimum natural or forced air or water circulation, depending on the system design) and usually such openings will be evenly spaced about the circumference or periphery of the holder body, as in FIGS. 1–3.

Figure 2:
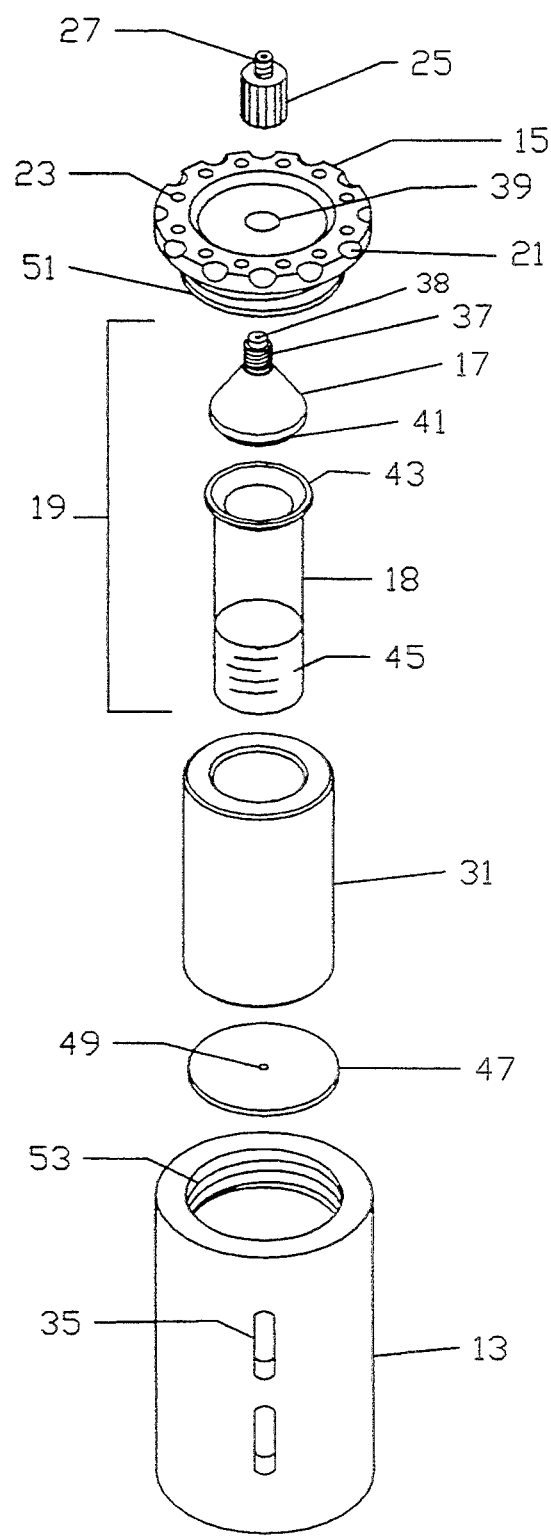
FIG. 2 is a disassembled view of parts of the apparatus of FIG. 1.

In FIG. 2 the various parts of the apparatus described in FIG. 1 are similarly identified and various other parts are described, too. Nipple 37, which extends upwardly and axially from the container cover 17, projects through opening 39 in holder cap 15 and screws into internally threaded fitting 25 so that tightening down of the holder cap 15 on holder body 13, after tightening of the nipple 37 into fitting 25 through opening 39, causes lower peripheral portion 41 of cover 17 to seal against upper nearly peripheral portion 43 of the container body portion 18, sealing off the container and its contents, represented by numeral 45. Reinforcement 31, which is of a suitable thermoplastic that melts at a relatively high temperature, such as PEI, and is reinforced at an interior portion thereof by continuous fibers, such as those of glass, in yarns which are braided, often preferably in sleeve form, fits inside holder body 13. Body 13 includes a bottom, not shown in FIG. 2, with an axial hole in it, also not so shown, and a disc 47, preferably of PEI or other suitable thermoplastic, sits on such bottom, with opening 49 therein aligning with the opening in the bottom of the holder body 13. Through such openings a pin may be inserted, after completion of a microwave heating of contents 45 and unscrewing of threads 51 of cap 15 from threads 53 of holder body 13, to promote release of the container body 18 from the reinforcement 31 by exertion of upward force on container bottom 55 through opening 56 in holder bottom 57 (both shown in FIG. 3).

Figure 3:
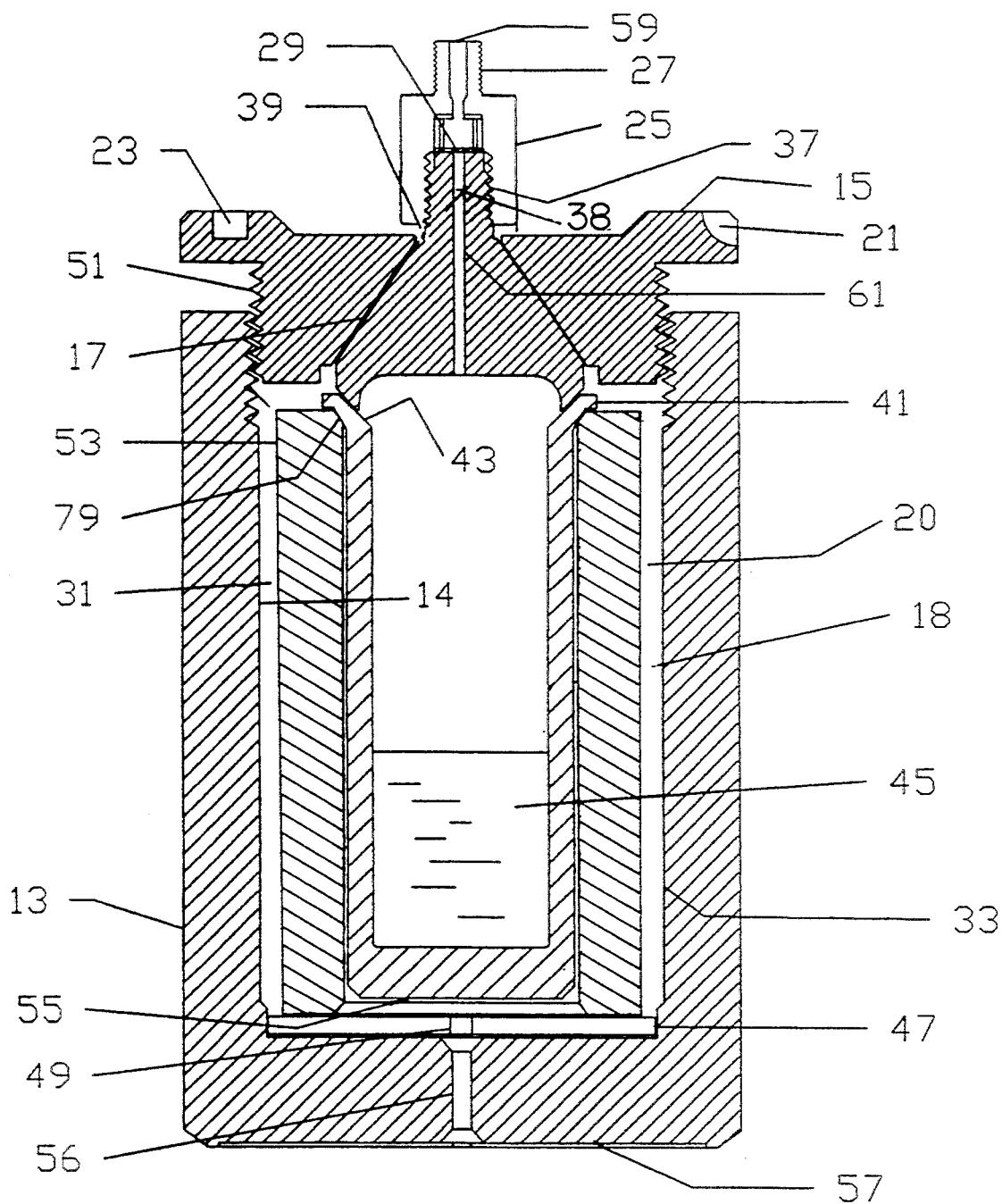
FIG. 3 is a central vertical sectional elevation taken along a vertical plane represented by 3—3 of FIG. 1.

FIG. 3 shows venting features of the invention that were not shown in FIGS. 1 and 2, although they were referred to in the description of such views. Because FIG. 3 is a sectional view it shows details of the invention that are not revealed or are not revealed as well in FIGS. 1 and 2. For example, the location and operation of the rupture disc is clearer from FIG. 3, wherein it is shown that such disc 29 seals off passageways 38 in nipple 37 and 61 in cover 17 during normal operation of the apparatus, but if subjected to more than the design pressure for the system it will rupture and allow venting of gas (and possibly some liquid too) through bore or passageway 59 in nipple 27 of fitting 25. Also, the details of the sealing of the container cover 17 to the container body 18 are better shown in FIG. 3, as is the clearance between reinforcement 31 and the interior surface 14 of holder body 13, which clearance is designated by numeral 33. As shown, it is relatively small but in practice it may be increased to provide better fluid circulation about the reinforcement for faster cooling of the container after completion of a digestion or extraction process. Clearance 20 is shown between container body 18 and reinforcement 31 but such clearance is usually only enough to allow for ease of disengagement of the container from the reinforcement after use of the apparatus, and the fit may be accurately "tight", e.g., about 0.001–0.05 inch.

Figure 4:
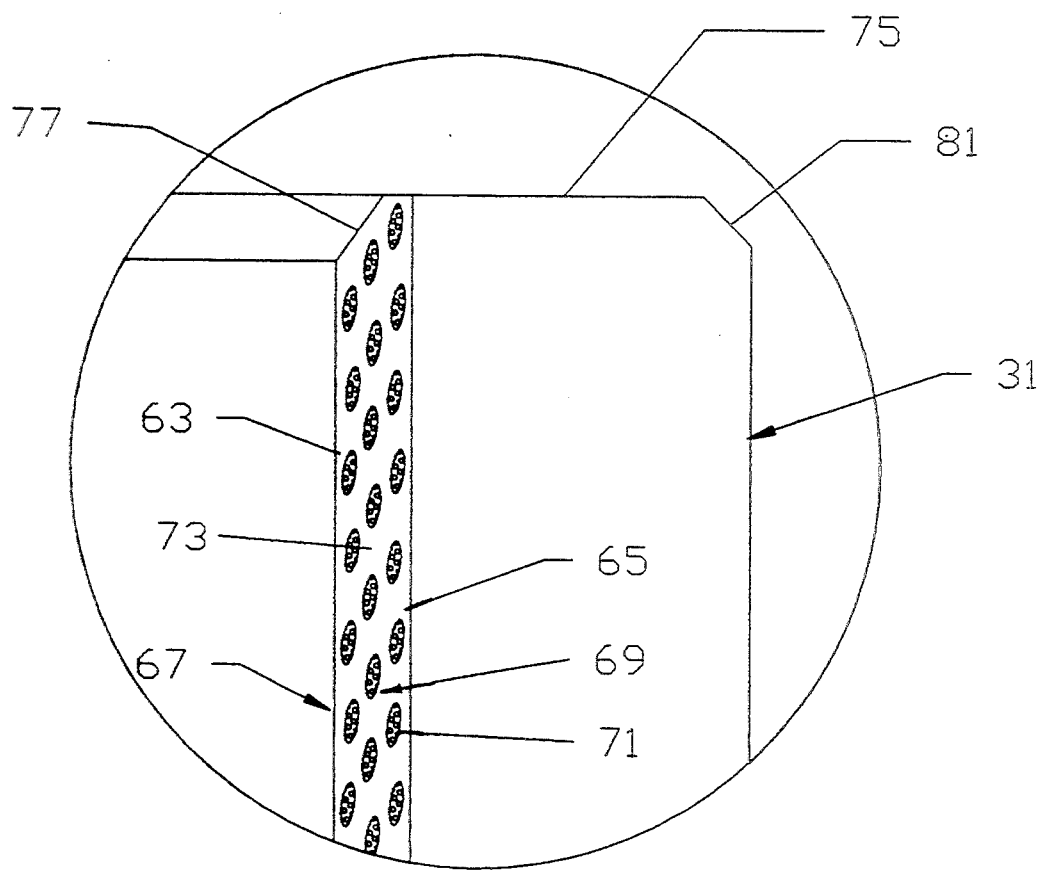
FIG. 4 is an enlarged central vertical sectional elevation of a portion of the cylindrical wall of the reinforced container of FIGS. 2 and 3, showing the reinforcing braid of glass yarn in the PEI matrix thereof.
Figure 5:
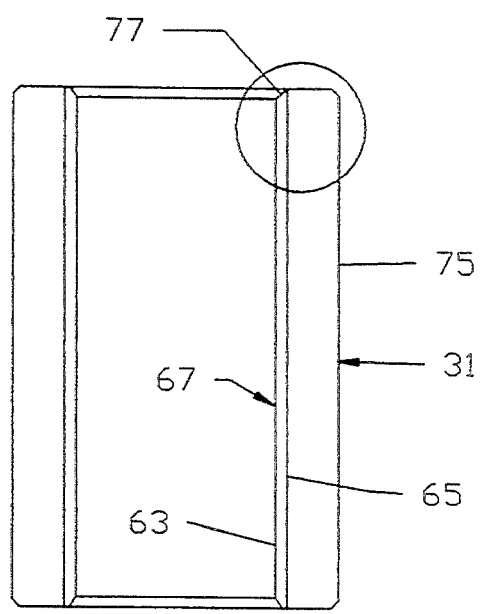
FIG. 5 is a central vertical sectional elevation of the reinforced container of FIGS. 2–4, in which the location of the FIG. 4 view is indicated.

FIG. 4 shows details of the construction of the part of the reinforcement 31 of FIG. 5 which is circled in both that figure and in FIG. 4. Reinforcement 31 includes a pure theremoplastic polymeric interior surface portion 63 (of PFA) and a similar exterior portion 65 of a tubular section 67, with the portion 69 between them including glass fiber or glass fiber yarn braiding 71 (three such braids being shown) in a matrix 73 of the thermoplastic. The tubular section 67 of the reinforcement 31, after being made by the process of the invention, has surrounding collar or sleeve part 75 of the reinforcement joined to it, preferably by injection molding of the portion 75 about it, to produce reinforcement 31. However, although it is preferred to surround the reinforced section 67 with pure thermopolymer, it is feasible to utilize as the reinforcement of this invention the tubular portion 67 without the surrounding pure polymeric sleeve.

In FIG. 4 a top internal bevel 77 is machined in the reinforcement interior wall to clear flange 79 (FIG. 3) of the container body 18. Also, a bevel 81 is shown at the top exterior of the reinforcement but such is optional and is not shown in FIGS. 1–3.

A sufficient description of the parts of FIG. 5 is found in the description of FIG. 4.

Figure 6:
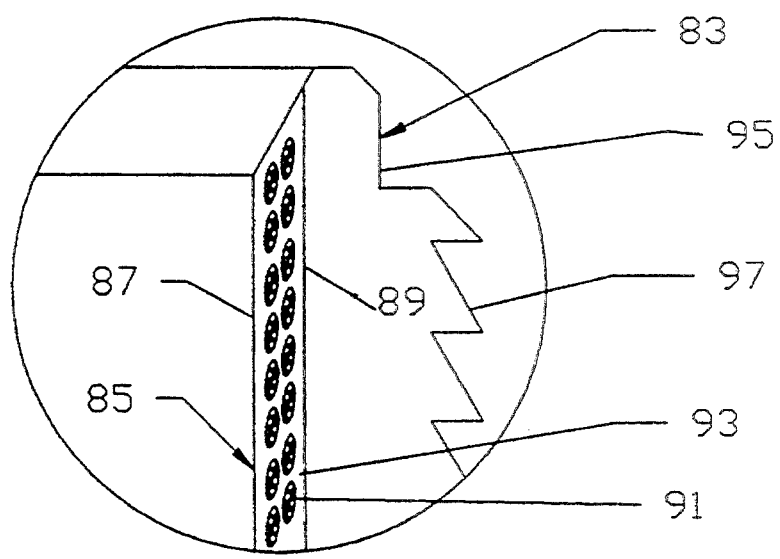
FIG. 6 is an enlarged central vertical sectional elevation of a portion of the cylindrical wall of a reinforced container of this invention, showing a fluoropolymer (PFA) inner wall section, continuous glass yarn or braid in a PEI matrix, and a PFA outer wall section, including a threaded portion thereof for fastening of a cover to the container.
Figure 7:
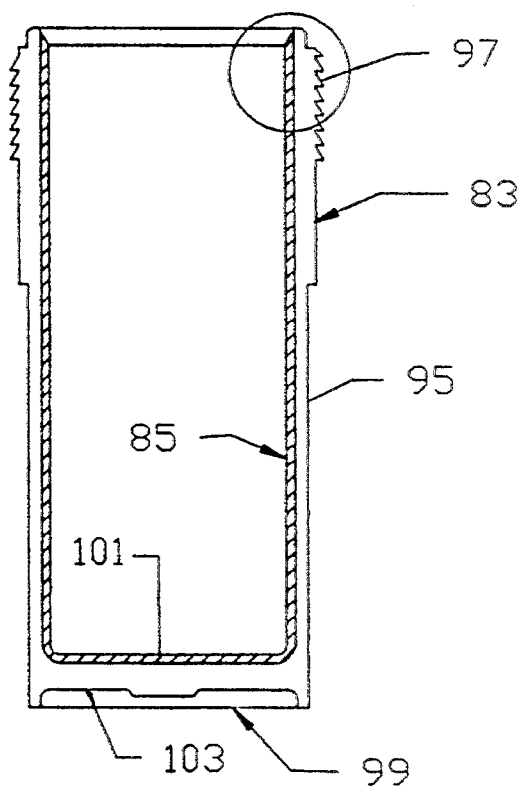
FIG. 7 is a central vertical sectional elevational view of the reinforced container of FIG. 6, in which the location of that view is indicated.

In FIG. 6 there are shown details of the construction of part of the container body 83 of FIG. 7 which is circled in both such figures. Such container includes an inner cylindrical side wall portion 85 comprised of an inner wall part 87 of reagent resistant thermopolymer, such as polyfluoroethylene, and an "outer" wall portion 89 of higher tensile strength thermopolymer, such as polyetherimide, with two braids 91 of yarns of glass fibers between them in a matix 93 of the polyetherimide. About the outer wall part 89 is molded a polyetherimide collar or sleeve 95 which includes molded in threads 97 for affixation thereto of an appropriate cover, not illustrated. Alternatively, and sometimes preferably, outer wall portion 89 may have sleeve 95 made of fluoropolymer instead of PEI so as to prevent contact of acid or solvent with the PEI.

In FIG. 7 container 83 has an integral bottom 99 comprised of integral inner and outer wall portions 101 and 103, respectively. Inner bottom wall portion 101 is made by the same general procedure as is followed for manufacturing cylindrical wall part 85, which will be described subsequently, but the braid or equivalent yarn structure is draped over the end of the mandrel with the thermoplastic sheets "interleaved" prior to heating and melting of the thermoplastic(s) into the yarn and/or fiber interstices to make the integral container, including a bottom. Then, the outer thermoplastic collar or sleeve 95 is injection molded about the reinforced container, and at the same time the threads 97 are formed and bottom 103 is molded integrally with the reinforcing means for the bottom and with the container side wall.

Figure 8:
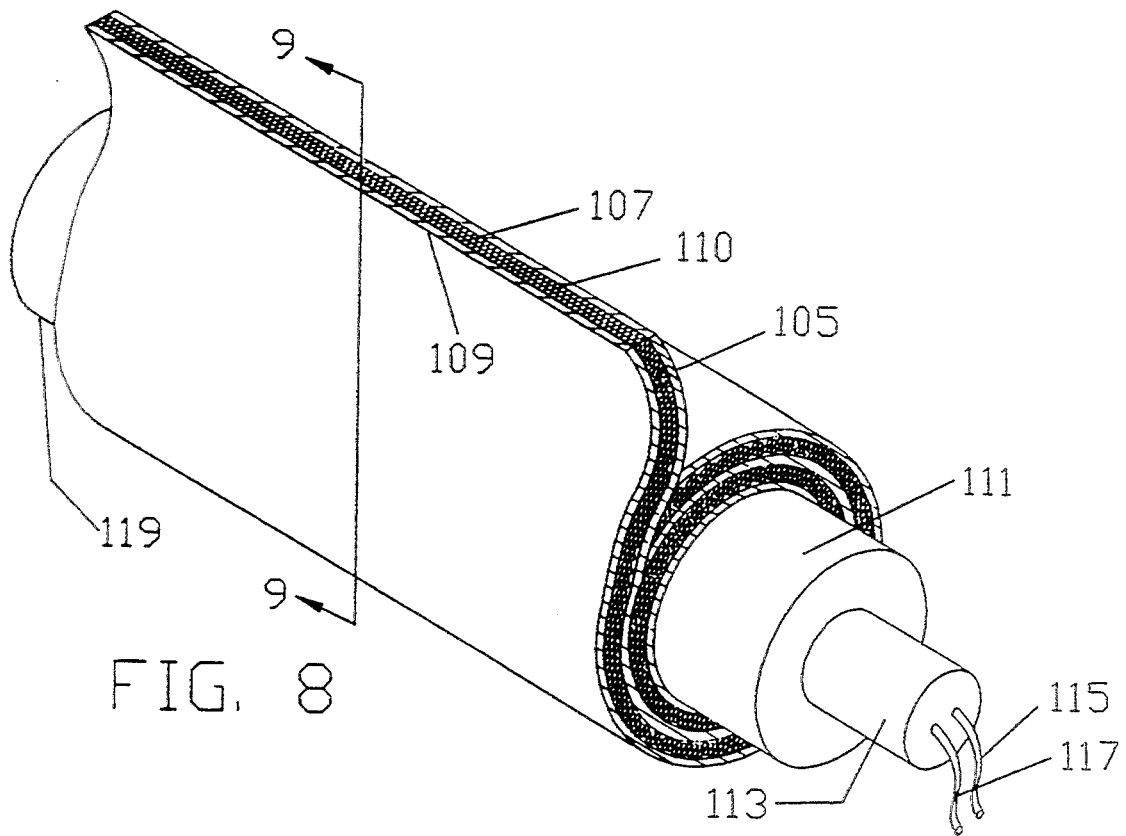
FIG. 8 is an isometric view of apparatus for manufacturing the reinforcement of FIGS. 1–5 by one of the processes described in this specification, with the thicknesses of different sections of the cylindrical wall of the reinforcement being exaggerated for clarity of exposition, and with sheets and braids of such materials being wrapped about a heating mandrel.

In FIG. 8 there are illustrated the essential parts of a simple apparatus for making reinforcing means of the invention which may be a reinforcement for a container or may be a wall (shown as cylindrical) of a container. In the illustration a cylindrical reinforcing means, like tube 67, is made by wrapping around a cylindrical mandrel in a "sandwich" 105, sheets 107 and 109 of thermoplastic polymer, such as fluoropolymer or PEI, about a braid or weave of continuous glass, quartz or aramid yarn 110. The wrapping may be of a single layer of the sandwich components or of several layers thereof and in one embodiment of the invention each sandwich may be of two sheets of polymer on each side of the fibrous material, with the outermost and innermost sheets being of fluoropolymer and adjacent sheets being of PEI. Similarly, other combinations of thermoplastic sheets may be employed instead. The ends of the wrapped sandwiches are then held to the under layers thereof and to the mandrel by application of pressure and the mandrel 111 is heated to a temperature at which the polymers melt, and is so held for a time sufficient to cause such melting and flow of the polymer(s) into the interstices of the braids, weaves and yarns of the fibrous material. Heating of the sandwich and application of compressive forces to them during heating tends to promote flow of the polymers, while at the same time compressing the fibrous "filling" of the sandwich, which tends to decrease the diameter of the reinforcing means at the seam, where any overlapping terminates. The mentioned compressive forces may be applied by any suitable means, such as shrink plastic wrapping or tapes, elastic bands (preferably with insulating bands between them and the sandwich, or by a clamping form. If there is no overlap of the sandwich (when it is pieced to fit exactly over the form) no such seaming problem will be encountered. Mandrel 111 is heated by an electric resistance heater element 113, which is internal of the mandrel and is connectable to a source of electric power by means of wires 115 and 117. After melting of the polymer(s) and filling of the fibrous material interstices by the melted polymers the electric power is shut off and the mandrel and covering sandwich are allowed to cool. During the heating operation the assembly is preferably held in an insulated container to promote even heating and maintenance of approximately the same temperature throughout the assembly, to avoid heterogeneity in the product and to produce the strongest reinforcing means. After cessation of maintenance of the assembly at elevated melt temperature it is cooled, either by ambient air or by other cooling means, to solidify the polymer(s), and the cooled assembly, upon solidification, is removed from the mandrel. It may then be trimmed at the ends thereof and is ready to be employed as a reinforcement for the digestion and evaporation containers, as illustrated in the drawing. Alternatively, the mandrel may be shortened or the sandwich may be lengthened so that the far end 119 of the mandrel is flush with the sandwich, and a bottom portion, in flat cup-like shape, not shown in this figure but illustrated in FIG. 11, may be fused to the cylindrically walled portion during the heating operation. Such flat cup may be formed integrally with the rest of the cylinder too and end 119 of the mandrel may be covered with a flat cup-shaped bottom portion that joins appropriately to the cylinder wall, with the layers of polymer being in a contact with the similar layers and with the reinforcement, like that shown in FIGS. 1–5. In another variation of the invention the container, with integral side wall and bottom, may be made of fluoropolymer and fibrous reinforcing means only, without the PEI, but such products will be of lesser resistance to failing under high pressure, high temperature applications.

Figure 9:
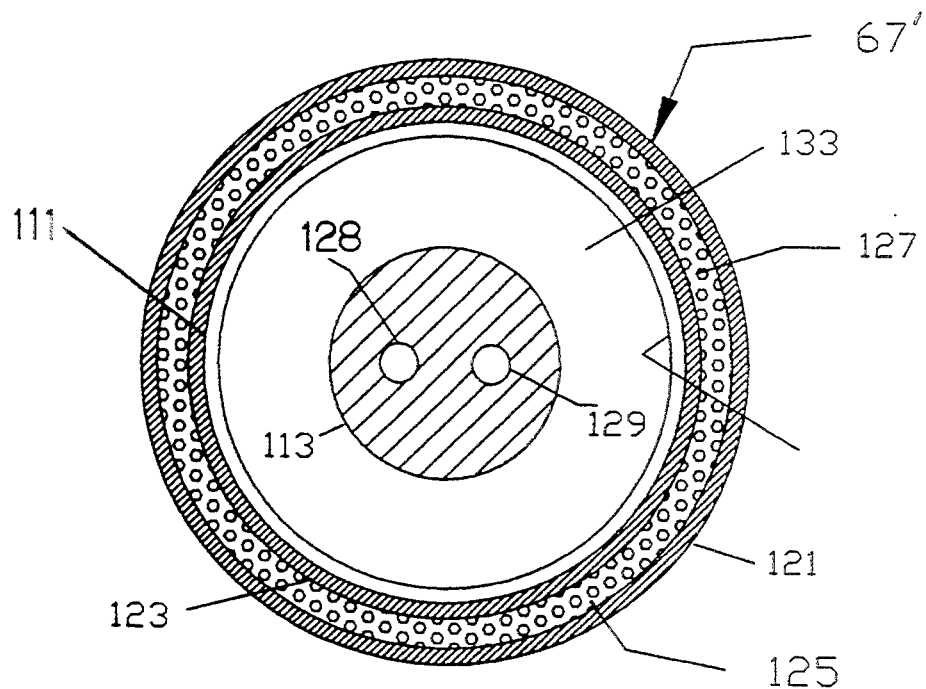
FIG. 9 is a transverse (to the longitudinal axis) sectional view, along plane 9—9 of FIG. 8, of the heating mandrel of FIG. 8, after cooling of the reinforcement about it, which view shows only a single sandwich of reinforced PEI between bounding layers of PFA.

FIG. 9 illustrates the mandrel of FIG. 8, with the finished reinforcement means about it, after completion of the cooling step. In this figure there is shown a single covering on the mandrel, which is tube 67', comprising outer thermoplastic covering 121, preferably of fluoropolymer, inner thermoplastic layer 123, also preferably of the same material, and "sandwich filling" 125, of high tensile strength thermoplastic, preferably PEI, with reinforcing continuous fibers, yarns, braid or weaves 127 therein. In the center of the mandrel 111 is located resistance heater 113, with its heating element portions 128 and 129. Location 133, between heater 113 and the inner wall 112 of mandrel 111 may be hollow or may be of conductive material (which is preferred).

In FIG. 10 schematically pictured injection mold portion 135 is shown, set up for molding of a collar or sleeve 75 (FIGS. 4 and 5) about tubular section 67. As illustrated, reinforced tube 67 is positioned in mold 135 about a mounting post 137 and liquid state thermoplastic polymer is injected into the cylindrical mold cavity 139 through port 141. When the mold is cooled and opened (opening seam is not illustrated) the resulting reinforcement, of a reinforced tube covered with thermopolymer (preferably with the thermopolymer of the tube being PEI and the thermopolymer of the covering collar or sleeve being PEI or fluoropolymer) may be removed, and will be a single integral reinforcement, ready for use.

FIG. 11 is essentially the same as FIG. 10 but illustrates the mold set-up for forming a collar or sleeve about a reinforced container of the invention. As is seen from a comparison of the figures the mold parts are the same but the collar or sleeve is molded about a reinforced container instead of about a bottomless cylindrical reinforcement unit. Container 143, the making of which was mentioned in the description of the apparatus of FIG. 8, is inverted and is positioned atop mounting post 137, and thermopolymer is injected into the mold through port 141. Among advantages of this operation and the resulting construction are that the container can have fluoropolymer or other thermopolymer that is resistant to material in the digestion or extraction mix enclosing such mix, thereby inhibiting attack on the container, and the sleeve or collar molded about the container gives it greater structural stability and mass, making it easier to use.

As had been previously indicated, a main object of the present invention is the provision of a reinforcing means for protecting a container so that it may be useful in operations in which it is subjected to high pressures and temperatures, usually in the presence of corrosive reagents, such as strongly acidic digesting liquids, or solvents. Such reinforcing means may be a separate reinforcement that prevents a container from bursting by restraining it against peripheral or radial expansion or it may be a part or all of the wall (and bottom) members of the container. It may also be the top of such container although in the digesting and extraction operations, which are the primary intended uses for the invention, separate tops or covers are usually employed, which are normally held to the container body by screw threads or other fastening means.

When the reinforcement is employed it will usually reinforce peripherally or radially a container made of acid and/or solvent resistant thermopolymer. Such polymer will be microwave transparent or essentially transparent, as is required for the various materials employed in this invention, which are to be exposed to microwave radiation that is to pass through them to the material to be digested, extracted or otherwise heated. While various thermopolymers can satisfy such conditions it has been found that the fluoropolymers, such as those sold under the TEFLON ® trademark, are better than most of the others, and of the various Teflons TEFLON PFA is the best. The Teflons are described in the *Chemical Engineering* article previously mentioned in this specification and they include PTFE (polytetrafluoroethylene), FEP (fluorinated ethylene propylene), PCTFE (polychlorotrifluoroethylene), ETFE (ethylene tetrafluoroethylene), ECTFE (ethylene chlorotrifluoroethylene), FVDF (polyvinylidene fluoride) and PFA (perfluoroalkoxy), of which it is considered that PFA is the best for the purposes of the prevent invention. Such fluoropolymers have tensile strengths greater than 2,000 lbs./sq. in. at their break points at room temperature and also have such tensile strengths greater than 1,000 lbs./sq. in. at 150° C. and also at 200° C.

Additionally, they have melting points and continuous heat resistant temperatures greater than 129° C., with PFA, PTFE, FEP and ETFE having melting points greater than 250° C. and PFA, PTFE and FEP having continuous heat resistant temperatures in excess of 200° C. Although the fluoropolymers are highly preferred materials of construction for the containers of this invention when separate reinforcements are employed, and are preferred for reinforcement and reinforced container inner and outer walls too, other thermoplastics, such as ABS, SAN, polyethylene, polypropylene, polycarbonate and injection moldable polyurethane may be employed instead, provided that they are compatible with the processes being practiced.

The polymeric materials that are useful for the matrix for the reinforcing fibers and yarns may be any that are thermoplastic and of sufficient strength and compatibility with the fibers to produce a strengthened composition and assembly under elevated temperature conditions of use. Such use will normally be either digestion or extraction but other operations may also be performed with the reinforced container assemblies of this invention. The thermoplastic will be microwave transmissive, with little or no objectionable absorption of microwave energy from the applied microwave radiation, which will normally be of a frequency in the range of 0.8 to 3 gigahertz. Usually, the tensile strength of the thermoplastic will be at least 1,000 lbs./sq. in. at 150° C., preferably at least 2,000 lbs./sq. in at 200° C. and more preferably about 5,000 lbs./sq. in. at such temperature, which temperature is often a maximum temperature or about the highest normal operating temperature for various digestion and extraction processes. Such processes, while capable of being used commercially, are often employed in connection with analytical and laboratory procedures.

Although various other thermoplastics that meet the criteria set forth above, or in some cases less stringent criteria, may be employed as the matrix for the reinforcing fibers of this invention, including polypropylene, ABS, polystyrene, fluoropolymers and polyacetals, it is highly preferred to employ a polyetherimide (PEI) as such matrix, largely because of its high tensile strength and its compatibility with reinforcing fibers, such as those of glass, quartz or aramid. They melt or have normal use temperatures, for extended periods of employment, which are at least 150° C. and often are at least 200° C., and when they are reinforced by the presence of reinforcing fibers and/or yarns in them their strength increases and their maximum continued use temperatures rises. Various grades of the mentioned thermopolymers can be employed but it will usually be preferable to select the purest of the high quality grades, with the highest tensile strength at elevated temperatures. In most cases that will be a preferred PEI, such as ULTEM 1000 or ULTEM 1010. The ULTEM's can contain chopped glass fibers (ULTEM's 2100, 2200, 2300 and 2400, for example) but it has been found that such compositions do not satisfactorily increase the radial or peripheral tensile strength of a reinforcing means because the short fibers, being discontinuous, do not impart as much strength to the reinforcing means as is wanted. With the continuous yarns of the present invention greater strength is obtained and the reinforcing fibers and yarns are oriented to provide the desired reinforcement against peripheral or radial rupture of the reinforced container wall.

The reinforcement material for the thermoplastic matrix of the present reinforcing means can be any that is suitable for the present purpose, which sufficiently increases the strength of the matrix material without absorbing objectionable proportions of microwave radiation, so that the protected container for material subjected to pressure during processing operations can withstand the process conditions, which include subjections to elevated temperatures and pressures. Of such materials that are commercially available the best are glass and aramid fibers. Quartz fibers and microfibers are also very good but are expensive and are impractical for many uses because of that fact. The fibers employed are normally of the E Glass or S Glass type, e.g., S-2 Glass, such as are available from Owens-Corning Fiberglas, Inc., but may also be of the aramid type, e.g., K-49 Aramid, available from DuPont. Such glass fibers have tensile strengths at 200° C. of at least 200,000 lbs./sq. in., which is about six times that of steel. The fiber or filament diameter of the glass and aramid will usually be in the range of 0.05 to 1.5 mm, preferably 0.1 to 1 mm, but sometimes, depending on the circumstances, greater and lesser diameters may be utilized. Although individual fibers can be employed as the reinforcing members, provided that they are positioned so as to take the strains to which the devices of the invention are subjected during use, it will usually be preferable for the fibers to be wound in yarns, which in turn, can be formed into braids, weaves or non-woven mats, which are normally the forms that are employed in the composite reinforcing means. The important thing is for a significant proportion of the fiber to be capable of holding a strain in the peripheral direction of the reinforcing means (which is at a right angle to the radius). To accomplish this the fibers or filaments of the braid or weave or other cloth or non-woven pad should desirably have an average component of at least 0.1 in such peripheral direction of strain (as distinguished from an axial component), preferably at least 0.2 (slope) and more preferably, at least 0.4 or 0.5, e.g., 0.7, which is that for a biaxial braid sleeve described in the working example herein. Of the various types of arrangements of the fibers in the thermoplastic material of the matrix it is preferred to employ biaxial braids for most satisfactory locating of the strengthening fibers with respect to the polymer. The resulting reinforced matrix material will have a tensile strength, at 200° C., that will be in excess of 25,000 lbs./sq. in., preferably more than 50,000 lbs./sq. in., and most preferably more than 75,000 or 100,000 lbs./sq. in. Still, other strengths of the reinforced thermoplastic may be used, depending on the circumstances. The greater the strength of the reinforced matrix the thinner the reinforced container can be made, while still being capable of withstanding any expected pressure that may be developed in the container during normal use thereof. Thus, for a very strongly reinforced composit, a comparatively thin container may be used, with greater ease of operation and handling, and in some such cases the rather massive holder pictured in the drawing accompanying this application may be omitted, with the reinforced container itself being its own protection and with a separately held cover being provided for it.

The holder, if employed to hold the cover onto the container to protect it against axial pressures and forces during use may be of any suitable thermoplastic (and of a suitable thickness) so that it can withstand the axial forces exerted on it during use, and so that it can hold the cover to the container during use. Of the various materials available for this purpose it has been found that polypropylene is the most satisfactory. It is not usually expected that the material of the holder should have to be capable of resisting acidic and solvent reactions because ideally none of the material being digested and extracted should contact it, but acid and solvent resistances are useful characteristics. Although they are expensive, Teflons and other fluoropolymers can satisfactorily act as holders, as can ABS and PEI's.

Various relatively minor parts of the invented assemblies may be made from available suitable thermopolymers, of which some that are preferred will now be described. The cover for the container will usually be of fluoropolymer, as will be the nipple on it. Fitting 25 is preferably made of polypropylene and disc 47, if present, will desirably be of PEI.

The different parts of the illustrated assembly of the holder and reinforced container, except for the reinforcing means, and sometimes the container too, may be made by normal manufacturing techniques. These involve injection molding and sheet stamping for the most part and while the making of the reinforcing means and the reinforced container can be effected by modified injection molding, a better product will usually result if it is produced from sheet polymer that has been sandwiched about a layer of fibrous reinforcing material. That procedure, in two different versions, both of which are operative to make excellent reinforcements for containers to be held at elevated temperature under pressure, will be described below.

First, a mandrel, like that shown in the drawing (FIGS. 8 and 9), is wrapped with a layer or more of a thermoplastic. Because PEI is a highly preferred such material for the present constructions it will be described herein but that should not be interpreted as limiting such aspect of the invention to polyetherimides only. The wrapping may be helically, as of a strip of tape about a cylindrical mandrel, or it may be of a strip of PEI sheet applied transversely and peripherally about the cylinder so that a single layer is created, with the longitudinal ends meeting at a seam. Alternatively, plural layers may be applied with overlapping, as is illustrated in FIG. 8. Next, the glass or other fibrous material is applied about the wrapping of the thermoplastic. As illustrated in FIG. 8, this application may be as a sandwich, which produces a "jelly-roll" effect. In another manufacturing procedure the yarn of glass fibers, in braid form (preferably) but sometimes in woven form, is slid onto the mandrel over the applied thermoplastic film and is drawn tight. Other techniques too may be employed to accomplish the desired result of the fiberglass evenly covering the under layer of PEI. An important consideration is that the reinforcing glass fibers should have an average fiber extending in the direction of the strain that will be peripherally exerted on them, with a slope of about 0.2 or more (of all the fibers), which is equivalent to at least 20% of the fibers extending peripherally, so that the fibers will be most effective in reinforcing the PEI. After application of the glass fibers to the PEI a further layer of PEI is applied to sandwich in the glass fibers, in the matrix of the PEI, and the entire sandwich is held steady on the mandrel before the flow of the PEI matrix about the mandrel to produce the desired reinforcement or container shape.

The melting of the PEI about the fiberglass and mandrel is effected by heating of the mandrel to the melting temperature of the PEI, which is about 300° C. (melting points of other useful thermoplastics are usually in the 200° to 400° C. range), and applying sufficient heat to raise the temperature of the PEI to its melting point, which is usually in the 250° to 350° C. range. The assembly is then held in place for from 1 to 30 minutes or an hour, or until the matrix is continuous within the fiberglass interstices, after which heating may be discontinued and the assembly may be cooled or may be allowed to cool. The result is a relatively thin tube of strengthened PEI, which may be trimmed as desired for use as a reinforcement for a container to be held under pressure. The mandrel size had been chosen so that the reinforcement made would fit the pressure container exactly, usually with only allowance being made for differential expansion and a small clearance, on the order of about 0.05 to 0.5 mm.

In some instances the reinforcement may have additional PEI injection molded about it, in the manner shown in FIG. 10, wherein only covering cylindrical and bottom portions are enclosed about the reinforcement but in other modifications, like that shown in FIG. 11, a bottomed reinforcement may have a sleeve or collar molded about it, for additional strength and/or ease of handling. In further modifications a polyfluoromeric thermoplastic of the TEFLON type, preferably TEFLON PFA, will be incorporated into a container as sheets during the forming process in the manner described above for the mandrel manufacture of the reinforcement but will be so constructed that the TEFLON sheet or coating will be on the container interior and exterior. Such construction will protect the container interior against any attack by strong acids and/or solvents and will also protect the container exteriors against attacks by spilled or escaped such material (it has been discovered that nitrogen oxides, from nitric acid digestant, can penetrate polymer walls). To make such containers, with cylindrical or equivalent walls, and bottoms, the bottom sections will be separately formed and fastened to the wall sections prior to melting of the PEI sheets, so that when the polymer cools to a solid an integral container will be formed. A certain proportion of overlap will often be desirable and in some instances fiberglass yarns from one part will be woven into the other part to promote better bondings between the parts, although this is usually unnecessary. In further embodiments of the invention instead of PEI sheets only being utilized as the "bread" about the fibrous filling in the sandwich such bread may be of both PEI and PFA sheets together, with the PFA on the innermost and outermost sides, where it can protect the PEI and the filling material against the effects of the digesting acids, etc.

In use, the invented assembly of container and reinforcement (or reinforced container only) is employed for digestions, extractions or other reactions or operations that might be conducted under pressure while the contained substance is being heated. Such an apparatus for the container parts thereof but not for any reinforcement, may be essentially like those of U.S. Pat. No. 5,230,865, but may be of various other designs and constructions too. The material to be treated and the reagent, digestant or extractant are charged to the PFA container and the container is connected to its protective apparatus, including a pressure probe, a rupture disc and other attachments, if appropriate, which connection is effected by fitting the cover onto the container and tightening the cap onto the holder. Then the microwave radiation of the holder-container assembly is begun, preferably onto the container in a microwave system equipped with oscillating turntable for even heating. The heating is continued long enough to accomplish the assigned task (which time is different for different operations but usually is within the period from 10 minutes to 2 hours). During the heating the pressure in the container may build up to as high as 5,000 lbs./sq. in. but will normally be no higher than 1,000 or 2,000 lbs./sq. in. and preferably is limited to about 500 lbs./sq. in. Because the maximum sustainable strain in use for the composites is about 75,000 lbs./sq. in., even if a safety factor of 3 was utilized to sustain an internal pressure in the container of 500 would take only 1/150 sq. in. of the reinforcement wall cross-section, or only a wall thickness 0.007 in. thick. Thus, it is clear that the reinforced material is capable of protecting the container against failure due to excessive internal pressure. Additionally, although no accidents have occurred in which the described containers, protected by the invented reinforcements, have not performed satisfactorily, even if that were to occur, any damage done would be limited, due to the nature of the reinforcements, which tend to part gradually, rather than in microseconds, when subjected to rupture pressures.

The following examples illustrate preferred embodiments of the invention but do not limit it. Unless otherwise indicated, all parts are by weight and all temperatures are in °C.

EXAMPLE 1

The apparatus illustrated in FIG. 8 is employed to make a reinforcement like that shown in FIGS. 2-5. To begin with, the mandrel is cleaned of any resin flashings and any other materials left from any previous operations, after which a mold release agent is applied to it. Such agent is preferably a silicone, with Mono-Coat E304 being the agent of choice, which is obtainable from Chem-Trend Inc. The release agent is useful to assist in easy removal of the molded item from the mandrel but may not be required in some instances, as when a peelably removable material, such as a suitable paper, is applied with the first sheet, sleeve or tape of PEI. It is also desirable to apply the mold release agent in amount to cover the mandrel completely, including the ends thereof and any exposed portions. After the release agent has dried on the mandrel surfaces the main cylindrical mandrel surfaces have shrink tape applied to them, with an overlap of the windings of about 0.1 in. Such shrink tape is a polyimide heat shrinkable tape which can withstand high temperature applications well and can shrink 12% of its length at 700° C. It is obtainable from Dunstone Company, Inc. as their HI-SHRINK POLYIMIDE. After application of the shrink tape it is coated with the release agent in the manner previously described and the release agent is allowed to dry.

The PEI (ULTEM 1000, obtainable from General Electric Company), in a sheet that is 0.007 in. thick, is cut to about mandrel length, which is about 40 inches, and is wrapped about the mandrel, making two revolutions (but more or less may be used, as desired, to give the thickness preferred), and the PEI film is held in place at the ends thereof with polyimide shrink tape, which is also held at the ends thereof with a pressure sensitive polyimide tape-(Airkap T.T, from Airtech International Inc.). Next, 1.5 inch diameter glass biaxial sleeving is cut to three lengths, with the first being 37 inches long, the second being 38.5 inches and the third being 40 inches in length. This sleeving is identified by the manufacturer, Atkins & Pearce Mfg. Co., as Medium Wall SM 1.50, is of E-Glass yarn (although S-Glass braids and weaves can be used too) and is of an areal weight of 23 ounces per square yard. The first braid is slid onto the mandrel over the resin sheeting (although the resin sleeve or sleeves could also be employed) without twisting thereof, and is pulled tight (axially) against the mandrel. The mandrel is then wrapped again with two layers of the Ultem 1000, taped with the shrink tape and held at the ends with the pressure sensitive tape in the same manner as before, and the second braid is slid on, which process is repeated again but with the third braid being slid on over the third Ultem film. Then the Ultem film is applied, as before, a light coat of mold release agent, the same as previously employed in this example, is applied and the assembly on the mandrel is spiral wrapped with polyimide shrink wrap tape (which may be Dunstone's Hi-Shrink Polyimide tape [or Kapton]), with a ⅓ inch overlap. A ¾ inch Watlow FIREROD ® Cartridge Heater, of 2500 watt power at 240 volts, which is 36 inches long, is inserted in the mandrel and the mandrel-heater assembly is placed in an insulated processing box which is shaped to fit the assembly. A thermocouple controller is employed to set and control the temperature to which the assembly is to be heated and the assembly is covered with an insulating blanket.

The thermocouple is set at 350° C. and after about 40 minutes of heating that temperature is reached, after which is held for an additional 20 minutes. The heater is then disconnected and the assembly is allowed to cool for ten minutes, with the insulating blanket off. Optionally, the assembly may be sprayed with a light mist of water to speed cooling. After the temperature of the formed part has fallen to 30° C. the mandrel and the part on it are removed from the insulated processing box and the heater is removed from the mandrel. Next, employing a hydraulic ram and a polypropylene bushing with an inside diameter slightly larger than the outside diameter of the mandrel, the mandrel is removed from the center of the formed part and then the shrink tape is removed from the part. The completed reinforced tube has non-uniform end portions cut off, using a tungsten carbide tipped saw blade, and the tube ends are sanded smooth. The parts are inspected for defects, such as excessive porosity, discontinuities and openings, and the parts that pass inspection are cut to desired lengths and are ready for molding onto them of collars or sleeves of PEI, when such additional features are desired.

The reinforcing means is mounted on a pedestal of an injection mold, as shown in FIG. 10, and melted PEI is injected into the mold about the reinforcing means, employing usual injection molding conditions. After cooling the reinforcement made, which is a composite of the reinforcing means tube and the enclosing PEI collar or sleeve molded onto it, which collar can have different features molded into it, such as knurls and threads, it is further machined, preferably using a diamond tipped cutting tool, and the part made is heat treated by heating to 150° C. for two hours. After completion of the heat treating (or annealing) the reinforcement is ready for use.

EXAMPLE 2

In an alternative manufacturing procedure, in which essentially the same reinforcement as described in Example 1 is made, the process of that example is changed by utilizing a sandwich or multiple layer sandwich of PEI and glass braid, in which the glass fiber is of a diameter in the range of 0.01 to 1 mm (but also can be micron sized). Instead of glass, quartz may be substituted. The yarns may be of 20 to 200 continuous fibers (or more or less, as desirable) and instead of a braid, woven yarns may be used or the fibers or yarns may be non-woven or extending primarily in the direction of the strain (peripheral). The two layers of PEI sheet, one layer of glass "cloth", two layers of PEI sheet, one layer of glass cloth, two layers of PEI sheet, one layer of glass cloth and two layers of PEI sheet, in the form of a sandwich or laminate, are wrapped as a unit around the mandrel and are held onto it under pressure, using the release agent, shrink wrap and adhesive, as described in Example 1, and as shown in FIGS. 8 and 9, and the reinforcement is made, with the collar of pure PEI injection molded onto it. Instead of shrink wrap and adhesive other means, such as clamping means may be utilized to exert sufficient pressure, e.g., 100 lbs./sq. in. on the assembly in the mandrel, so as to hold it tightly in place during the melting and cooling operations.

EXAMPLE 3

The procedures of Examples 1 and 2 are followed substantially in the processes of this example but both the interior and exterior of the tube made are of fluoropolymer (PFA) instead of PEI, so as to be more resistant to reagents that can be encountered during use there of, and the collar or sleeve of pure PEI is omitted. To accomplish this, two layers of fluoropolymer are applied to the mandrel before the PEI layers and two fluoropolymer layers are applied after the last PEI layers, with the processes otherwise being identical. The PFA melts at about the same temperature as the PEI so there is no heterogeneity caused by different physical states of the polymers during processing. Also, the polymers tend to join together well without the PEI migrating to the exterior or interior surfaces of the articles made, where it might be subject to attack by digestants or extractants, such as nitric acid or methylene chloride.

EXAMPLE 4

Bottomed reinforcements are made by the Example 1 process but with additions oft he bottom members to the tubes made by the process of that example. In the modification of the Example 1 process a circular sandwich, of as many layers of PEI sheet and fiberglass braid as the tube, is made to be held to a flush end of the mandrel, which end is also heatable. It is installed on that end, is interleaved with the layers of PEI and glass fiber material on the mandrel cylindrical surfaces and is held firmly in place so that on heating and subsequent cooling an integral bottomed reinforcement is made.

EXAMPLE 5

Bottomed reinforcements of the type described in Example 4 are made by a process which is a modification of the process of Example 2. In this example the bottom sandwich may be a circular cutout from the same composite sheet as is used to cover the mandrels' cylindrical surface. The bottom composite, corresponding to the mandrel end, is interleaved with the cylindrical side laminate and the resins of both are melted and cooled together to form an integral bottomed reinforcement.

EXAMPLE 6

In other variations of the manufacturing processes fluoropolymer-lined containers, which are of integral reinforced wall-bottom constructions, are made by the procedures described in Example 3, beginning the wrappings of the mandrels with two layers of fluoropolymer sheet, each about 0.010 inch thick, and ending the wrappings with another two layers of the same fluoropolymer (Teflon PFA 340 or 350). The integral bottoms are formed on the tubes, making the containers, by the procedure described in Example 4. In further variations of such processes the fluoropolymer replaces the PEI of Examples 1–3 and is itself reinforced by the fiberglass. While such reinforcing means and containers are improvements over those made from unreinforced fluoropolymer, they are not of the high pressure resistant properties of the PEI reinforced reinforcing means, so their uses may be limited to lower pressure operations.

EXAMPLE 7

In the procedures described in Examples 1–6 the materials of construction may be varied, with the substitution of other thermopolymers for the PEI and PFA, as described in the specification. Also, processing conditions may be varied, depending on the materials being employed and the equipment available. Other means for shaping the reinforcing means may be employed than those described and the reinforcing means and containers may be made in shapes other than cylindrical. For example, instead of utilizing fiberglass reinforcements, aramid fibers, such as fibers and yarns of KEVLAR ®, e.g., Kevlar 29 and Kevlar 49, or quartz may be the reinforcing continuous fibrous component of the reinforcing means and the matrix may be ABS or a different PEI, e.g., Ultem 1010. The reinforcing means and containers made are also useful in microwave extractions and other laboratory and commercial operations, wherein containers for the materials being processed are under pressure.

EXAMPLE 8

A digestion apparatus of the type described in Examples 1–5 is employed to digest corn oil in nitric acid. The digestion container is of PFA (Teflon PFA 340), is 4¼ inches tall, 1⅜ inches outside dia. and is reinforced by a reinforcement which comprises a fiberglass reinforced PEI tube that fits the container exterior, with a clearance of about 0.005 to 0.010 inch, and is of a thickness of about 1/16 inch with a PFA collar about it that is about ⅛ inch thick. The reinforced PEI tube is made by the procedure described in Example 2. 20 Replications of a digestion of 0.5 g of corn oil in 10 ml of 10% nitric acid are run, with the digestion temperature being raised to 200° C. and maintained there for a half hour in each case. The pressures developed average about 600 lbs./sq. in. and the microwave apparatus is operated at about 50% of its maximum power (operation at 600 watts). In no case does the rupture disc fail (it is set to fail at about 2,000 lbs./sq. in.) and in no instance does the PFA container fail or show signs of incipient failure. In separate testing, using hydrostatic pressure, the reinforced container (with the Example 2 reinforcement about the PFA container) withstands pressure of 600 lbs./sq. in. at 200° C. without failure. Such results are also obtainable (and the containers can withstand much higher pressures, up to 5,000 lbs./sq. in. at 200° C., without failure) in other digestion and extraction operations and with other apparatuses of this invention.

The invention has been described with respect to illustrations and examples of some preferred embodiments thereof but is not to be considered as limited to them because one of skill in the art will be able to utilize substitutes and equivalents without departing from the invention.

What is claimed is:

1. A container unit for heating a material by microwave radiation, comprising:
   a substantially cylindrical container for holding a material;
   a means for reinforcing said container, said reinforcing means being adapted to contain and fit around said container, said reinforcing means comprising a microwave transmissive layer of polyetherimide and a microwave transmissive layer of fluoropolymer, said polyetherimide layer having a continuous reinforcing fibrous material so located therein as to increase tensile strength thereof to at least 30,000 lbs./sq. in. in order to prevent rupture of the container at temperatures up to 150° C. and internal container pressures up to 500 lbs./sq. in. gauge, wherein said fibrous material is selected from the group consisting of glass, aramid and quartz fibers; and
   a polypropylene holder adapted to contain said reinforcing means and said container.

* * * * *